(12) United States Patent
Nomura (10) Patent No.: US 11,869,653 B2
(45) Date of Patent: Jan. 9, 2024

(54) INFORMATION PROCESSING APPARATUS, MEDICAL INFORMATION MANAGEMENT SYSTEM, AND INFORMATION PROCESSING METHOD

(71) Applicant: KONICA MINOLTA, INC., Tokyo (JP)

(72) Inventor: Seiji Nomura, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 696 days.

(21) Appl. No.: 16/986,310

(22) Filed: Aug. 6, 2020

(65) Prior Publication Data
US 2021/0065883 A1 Mar. 4, 2021

(30) Foreign Application Priority Data
Aug. 29, 2019 (JP) .................................. 2019-156251

(51) Int. Cl.
G16H 15/00 (2018.01)
G16H 30/20 (2018.01)
G16H 30/40 (2018.01)
G06F 16/51 (2019.01)

(52) U.S. Cl.
CPC ............. *G16H 30/40* (2018.01); *G06F 16/51* (2019.01); *G16H 15/00* (2018.01); *G16H 30/20* (2018.01)

(58) Field of Classification Search
CPC ........ G16H 30/40; G16H 15/00; G16H 30/20; G06F 16/51
See application file for complete search history.

(56) References Cited

U.S. PATENT DOCUMENTS

2010/0088113 A1* 4/2010 Kubota .................. G16H 30/20
382/128

FOREIGN PATENT DOCUMENTS

| JP | 2002109056 A | * | 4/2002 |
| JP | 2002109056 A | | 4/2002 |
| JP | 2009254690 A | * | 11/2009 |
| JP | 2009254690 A | | 11/2009 |
| JP | 2012183203 A | * | 9/2012 |
| JP | 2012183203 A | | 9/2012 |

OTHER PUBLICATIONS

Bui et al., "openSourcePACS: An Extensible Infrastructure for Medical Image Management," IEEE Transactions on Information Technology in Biomedicine (vol. 11, Issue: 1, pp. 94-109) (Year: 2007).*
Japanese Office Action (and English language translation thereof) dated Jan. 17, 2023, issued in counterpart Japanese Application No. 2019-156251.

* cited by examiner

Primary Examiner — Joshua B Blanchette
(74) Attorney, Agent, or Firm — Holtz, Holtz & Volek PC (57) ABSTRACT

An information processing apparatus that sends and receives data to and from an image storage apparatus that manages a medical file for each examination includes a first hardware processor. The first hardware processor generates image data from character information included in a non-image file related to examination, attaches examination information related to the non-image file to the generated image data, and creates a file converted to image. The first hardware processor further sends the created file converted to image to the image storage apparatus.

8 Claims, 12 Drawing Sheets

```
;*******************
;
;       SC_RT_ION_BEAMS_TREATMENT_RECORD_STORAGE
;
;*******************
;
[1.2.840.10008.5.1.4.1.1.481.9]

Enable = 1

; P TAG IS REQUIRED TO PERFORM PROCESSING AFTER SC CONVERSION
; ADDITION OF P TAG MAY BE OMITTED AND MAY BE PERFORMED ONE BY ONE
; WHEN ION, NUMBER OF SQItems OF 3008,0021-3008,0041 IS OUTPUT AS SC IMAGE
RootPrivateTag          =4001,1000                              — 71
NumberLeafPairs         =3008,0021-3008,00A0-300A,00BC
; MULTIPLE BELOW                                                — 72
BeamDeviceType          =3008,0021-3008,0041-300A,011A(n)-300A,00B8
LeafPositions           =3008,0021-3008,0041-300A,011A(n)-300A,011C — 70

— 74
; ACTUAL SIZE OF Multi Leaf Collimator     ( X,Y mm )
MlcRealSize      =      150,150

; DRAWING SIZE OF Multi Leaf Collimator    ( X,Y pixcel )
MlcDrawSize      =      160,160
                                                                — 73
; DRAWING POSITION OF Multi Leaf Collimator
MlcDrawPoint=           330,305
                                                                — 75
; COLOR OF ONE SIDE OF LEAF
LeafColorMaster = 210,105,30

; COLOR OF OPPOSITE SIDE OF LEAF (WHEN OMITTED, SAME COLOR AS Master)
LeafColorSlave   = 210,105,0
```

| | | | | |
|---|---|---|---|---|
| ⊞ | (3008,0060) | INVALID SEQUENCE | SQ | |
| ⊞ | SequenceItem01 | | | |
| | (0008,1070) | OPERATOR NAME | PN | == |
| | (300A,0015) | NOMINAL BEAM ENER... | CS | MEV_PER_NUCLEON |
| | (300A,0114) | NOMINAL BEAM ENERG | DS | 400 |
| | (300A,0115) | DOSE RATE SET | DS | |
| | (300A,011A) | BEAM LIMITING DEVICE POSIT... | SQ | |
| ⊞ | SequenceItem01 | | | |
| | (300A,00B8) | RT BEAM LIMITING DEVI... | CS | MLCX |
| | (300A,011C) | LEAF POSITION | DS | -81.2*-81.2*-81.2*-81.2*-81.2*-81.2*-81.2*-81.2*-81.2*-81.2*-81.2*-81.2*-81.2*-81.2*-81.2*-81.2*-81.2* |
| | (300A,011E) | GANTRY ANGLE | DS | 0.0 |
| | (300A,011F) | GANTRY ROTATION DIRECTION | CS | NONE |
| | (300A,0120) | BEAM LIMITING DEVICE ANG. | DS | 95.0 |
| | (300A,0121) | BEAM LIMITING DEVICE ROTA... | CS | NONE |
| | (300A,0122) | PATIENT SUPPORT ANGLE | DS | 10.0 |
| | (300A,0123) | PATIENT SUPPORT ROTATION... | CS | NONE |

INFORMATION PROCESSING APPARATUS, MEDICAL INFORMATION MANAGEMENT SYSTEM, AND INFORMATION PROCESSING METHOD

CROSS-REFERENCE TO RELATED APPLICATIONS

The entire disclosure of Japanese Patent Application No. 2019-156251 filed on Aug. 29, 2019 is incorporated herein by reference in its entirety.

TECHNOLOGICAL FIELD

The present disclosure relates an information processing apparatus, a medical information management system, and an information processing method.

DESCRIPTION OF RELATED ART

In a medical field, when a patient is imaged by an examination device, an image file of an examination image is output from the examination device. When the image file of the examination image is stored in an image storage device, the examination image can be displayed on an image viewer.

Regarding a medical image storage device that sends medical image data so as to be displayed on an image viewer, there has been proposed a technique for reducing the amount of medical image data as a whole, for example, by setting resolution in a predetermined portion of the image higher than that in the other portions based on an analysis result in a computer-aided diagnosis unit (see JP 2009-254690 A).

Furthermore, there has been used an image storage device that deletes a diagnostic image at the time of receiving a corresponding diagnostic image that has been used for image interpretation so as to store only the image used for image interpretation (see JP 2002-109056 A).

The data output from the examination device that carries out examination on a patient includes not only image data but also non-image data. The non-image data (such as treatment plan information that describes the treatment plan for the patient and dose information that indicates the amount of radiation irradiated to the patient at the time of examination/treatment) is output as a non-image file without image data.

SUMMARY

However, an image viewer that displays an examination image file in a DICOM (Digital Image and Communications in Medicine) format cannot display a non-image file such as treatment plan information and dose information. Therefore, an operator is forced to perform complicated operation to display the non-image file, such as operation of a viewer other than the image viewer. Furthermore, the non-image file tends to be overlooked because the non-image file cannot be confirmed in the same screen as the examination image file. At the same time, the non-image file displayed in a screen separately from the examination image file may interfere with browsing the examination image file.

The present invention has been made in view of the above-described problems and situations, and an object of the present invention is to make it possible to manage the non-image file related to the examination in association with the relevant examination.

To achieve at least one of the abovementioned objects, according to an aspect of the present invention, an information processing apparatus that sends and receives data to and from an image storage apparatus that manages a medical file for each examination includes:

a first hardware processor that:

generates image data from character information included in a non-image file related to an examination, attaches examination information related to the non-image file to the generated image data, and creates a file converted to image; and sends the created file converted to image to the image storage apparatus.

To achieve at least one of the abovementioned objects, according to another aspect of the present invention, a medical information management system includes:

an information processing apparatus according to an aspect of the present invention; and the image storage apparatus, wherein the medical file managed by the image storage apparatus includes an examination image file that is taken in the examination on a patient and the file converted to image that is created by the information processing apparatus, and the image storage apparatus includes a second hardware processor that causes the examination image file and the file converted to image corresponding to an examination selected via an operation unit to be displayed in a same screen of a display.

To achieve at least one of the abovementioned objects, according to another aspect of the present invention, an information processing method that is performed in an information processing apparatus that sends and receives data to and from an image storage apparatus that manages a medical file for each examination, the method comprising:

generating image data from character information included in a non-image file related to an examination, attaching examination information related to the non-image file to the generated image data, and creating a file converted to image; and sending the created file converted to image to the image storage apparatus.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein:

FIG. 8 shows an example of layout information;

DETAILED DESCRIPTION OF THE EMBODIMENTS

Hereinafter, one or more embodiments of the medical information management system according to the present invention will be described with reference to the drawings. However, the scope of the present invention is not limited to the disclosed embodiments or illustrated examples.

In the present invention, an examination means checking for suitability (whether a sample or an image is suitable as an examination target), whether or not there is any abnormality or dysfunctionality. Examples of the examination include an image diagnostic examination and the like.

A medical file is a file related to medical care. Examples of the medical file include a file of an image taken in the examination on a patient, a file including a numerical value measured in the examination on a patient, a file including various examination conditions, a file of a medical record, and the like.

An image file is a file that includes image data and header information that is supplementary information of the image data. The image file is, for example, a DICOM image file that is composed of DICOM image data and the header information that is supplementary information of the DICOM image data.

A non-image file is a file that does not include image data. An example of the non-image file is a non-image file composed of a DICOM header only. The non-image file includes treatment plan information, dose information, report information, order information, and the like.

Character information is a value(s) of a predetermined item(s) included in the non-image file. Examples of the character information include patient ID, patient name, sex, date of birth, age, examination date, examination time, modality, various examination conditions, examination results, treatment date, treatment time, various treatment conditions, and the like.

The image data is data converted to an image. Examples of the image data include DICOM image data and the like.

Examination information is information about the examination.

A file converted to image is a file in which examination information related to the non-image file is attached to the image data generated from the character information included in the non-image file.

Figure 1:
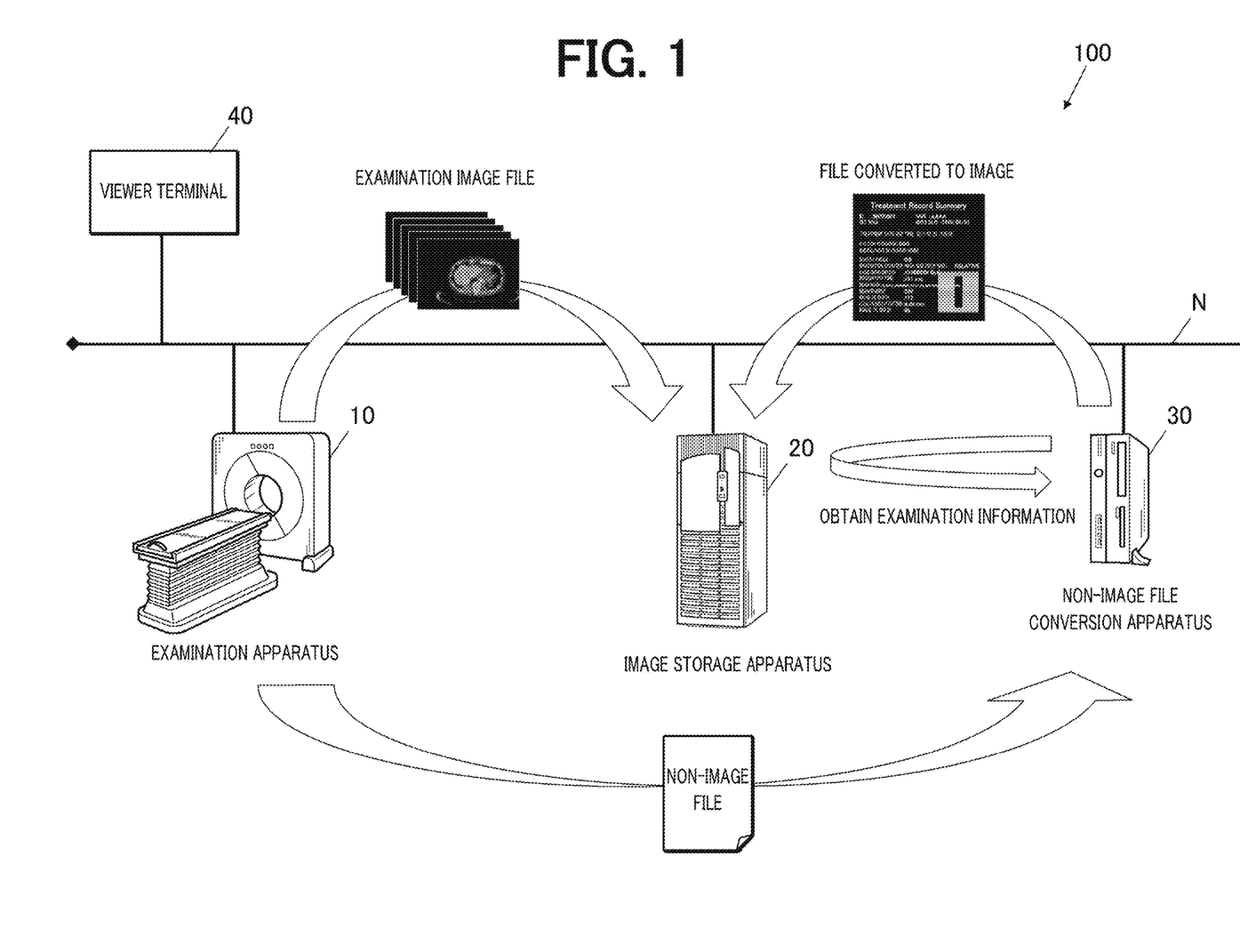
FIG. 1 is a diagram showing an example of a system configuration of a medical information management system according to an embodiment(s) of the present invention.

FIG. 1 shows an example of a system configuration of a medical information management system 100.

As shown in FIG. 1, the medical information management system 100 includes an examination apparatus 10, an image storage apparatus 20, a non-image file conversion apparatus 30 as an information processing apparatus, a viewer terminal 40, and the like that are connected to one another so as to send and receive data via a communication network N such as a LAN (Local Area Network) or a WAN (Wide Area Network). The apparatuses constituting the medical information management system 100 are in conformity with HL7 (Health Level Seven) standard and DICOM standard, and communicate with one another in accordance with the HL7 standard and the DICOM standard.

The examination apparatus 10 is a modality such as an X-ray imaging apparatus (DR, CR), an ultrasonic diagnostic apparatus (US), a CT, or an MRI, and generates image data of an examination image by photographing a patient. The examination apparatus 10 adds supplementary information to the examination image by writing the supplementary information (patient information, examination information, or the like) in a header of the image file of the examination image according to the DICOM standard, thereby generating the examination image file according to the DICOM standard. The examination image file is sent to the image storage apparatus 20 and is stored and managed in the image storage apparatus 20.

Figure 2A:
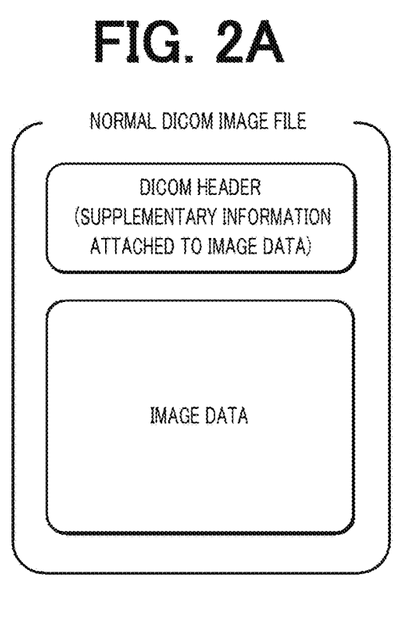
FIG. 2A is a diagram showing a configuration of a normal DICOM image file.

FIG. 2A shows a configuration of a normal DICOM image file. The DICOM image file is composed of image data and the DICOM header that is supplementary information of the image data.

Figure 2B:
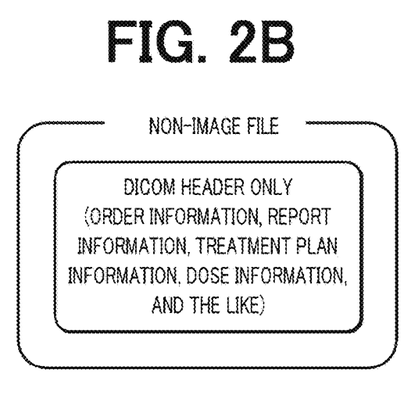
FIG. 2B is a diagram showing a configuration of a non-image file.

Some examination apparatuses 10 generate a non-image file including no image data, other examination apparatuses 10 may generate both the examination image file and the non-image file.

FIG. 2B shows a configuration of the non-image file consisting of the DICOM header only.

The image storage apparatus 20 manages, for each examination, a medical file in a DICOM format related to the examination. The image storage apparatus 20 stores the examination image file generated in the examination apparatus 10 and the file converted to image created in the non-image file conversion apparatus 30, and stores and manages them for each patient and for each examination. The image storage apparatus 20 is, for example, a PACS (Picture Archiving and Communication System).

Figure 3:
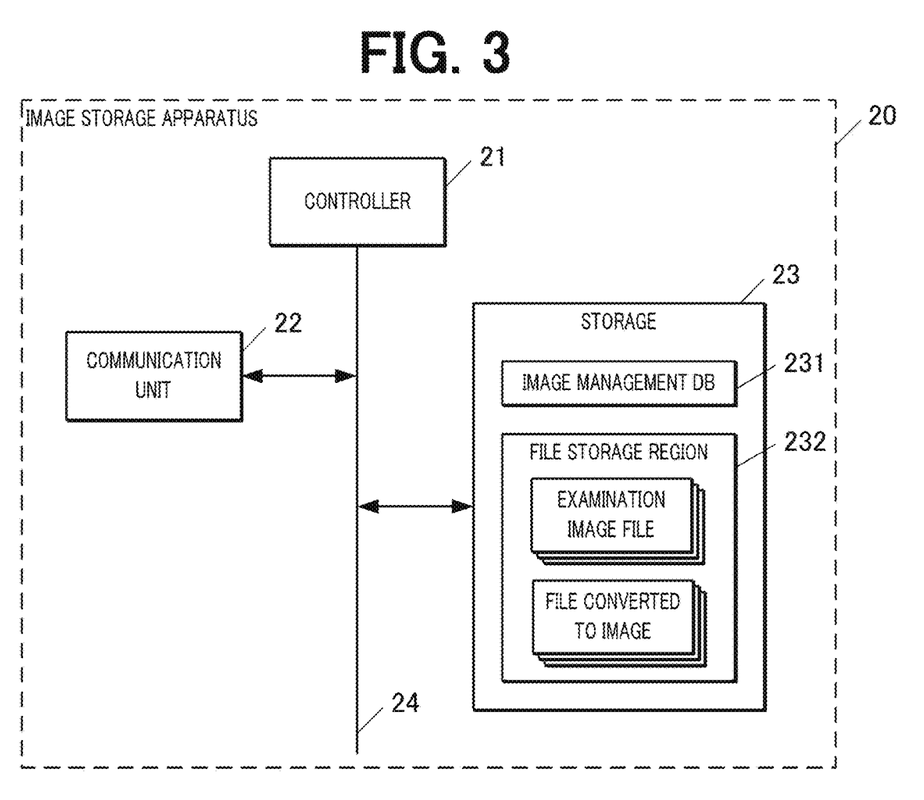
FIG. 3 is a block diagram showing a functional configuration of an image storage apparatus.

FIG. 3 shows a functional configuration of the image storage apparatus 20.

As shown in FIG. 3, the image storage apparatus 20 includes a controller 21 (second hardware processor), a communication unit 22, a storage 23, and the like, and these components are connected to one another via a bus 24.

The controller 21 includes a CPU (Central Processing Unit), a ROM (Read Only Memory), and a RAM (Random Access Memory) and comprehensively controls operation of each component of the image storage apparatus 20. Specifically, the CPU reads out various programs stored in the ROM, loads them into the RAM, and performs various processes in accordance with the programs.

The communication unit 22 is constituted by a network interface or the like, and sends and receives data to and from an external apparatus(es) connected via the communication network N. For example, the communication unit 22 receives the examination image file of a patient obtained by the examination apparatus 10 that photographs the patient. Furthermore, the communication unit 22 receives the file converted to image that is created by the non-image file conversion apparatus 30.

The storage 23 includes an HDD (Hard Disk Drive), a non-volatile memory, and the like, and stores various kinds of data. The storage 23 stores an image management DB (DataBase) 231. The storage 23 has a file storage region 232.

In the image management DB 231, the supplementary information (header information) of files is searchably stored for each medical file stored in the file storage region 232. The supplementary information includes patient information, examination information, series information, and image information.

The patient information includes a patient ID, a patient name, birth date, sex, and the like. The patient ID is identification information for specifying the patient.

The examination information includes an examination instance UID, the examination date, the examination time, and the like. The examination instance UID is identification information that is assured to specify the examination uniquely according to the DICOM standard.

The series information includes a series instance UID, the modality, portion, and the like. The series instance UID is identification information that is assured to specify the series uniquely according to the DICOM standard.

The image information includes an SOP instance UID, date and time of generation, a direction in taking image, a file path indicating where the file is stored, and the like. The SOP instance UID is identification information that is assured to specify the medical file uniquely according to the DICOM standard.

The medical file is stored in the file storage region 232. The medical file includes the examination image file received from the examination apparatus 10 and the file converted to image received from the non-image file conversion apparatus 30.

Figure 4:
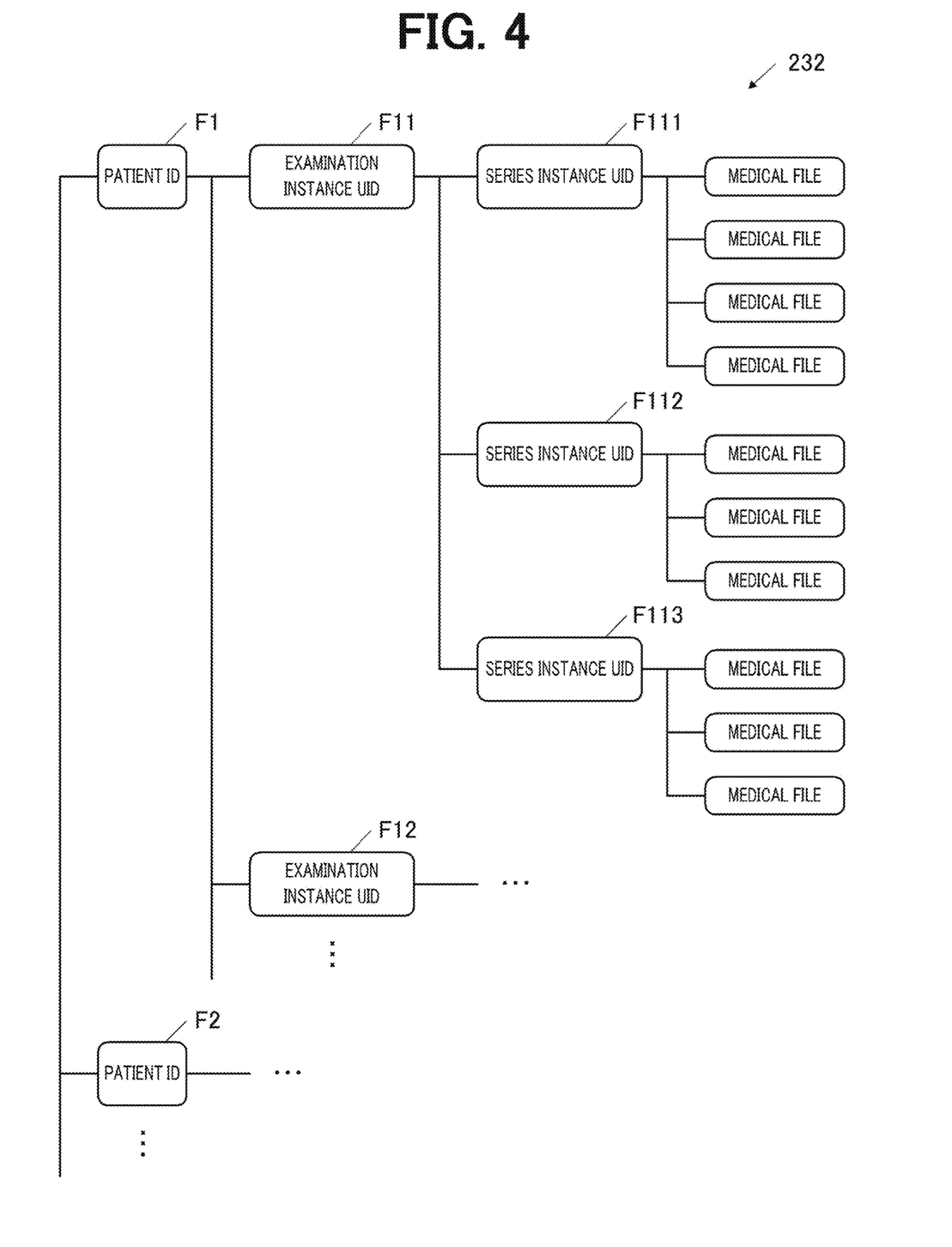
FIG. 4 is a diagram showing a folder configuration where data is stored in a file storage region.

FIG. 4 shows a folder configuration where data is stored in the file storage region 232 of the storage 23. The data is stored in respective folders that form a layer structure and are arranged in the order of patient, examination, and series.

Specifically, "patient ID" folders F1, F2, . . . are created for respective patients.

In a folder layer under the "patient ID" folder F1, "examination instance UID" folders F11, F12, . . . are created for respective examinations. "Examination instance UID" folders are similarly created under each of the "patient ID" folders corresponding to other patients as well.

In a folder layer under the "examination instance UID" folder F11, "series instance UID" folders F111, F112, F113 are created for respective series. "Series instance UID" folders are similarly created under each of the "examination instance UID" folders corresponding to other examinations as well.

The "series instance UID" folders each store the medical file.

The number of files stored in each "series instance UID" folder is not limited to the illustrated example.

Because the patient ID is not assured to specify the patient uniquely according to the DICOM standard, there may be no patient folder layer specified by the patient ID in some systems.

In response to a request of the viewer terminal 40 via the communication unit 22 to obtain a medical file, the controller 21 sends screen data to display the requested medical file to the viewer terminal 40.

Figure 6:
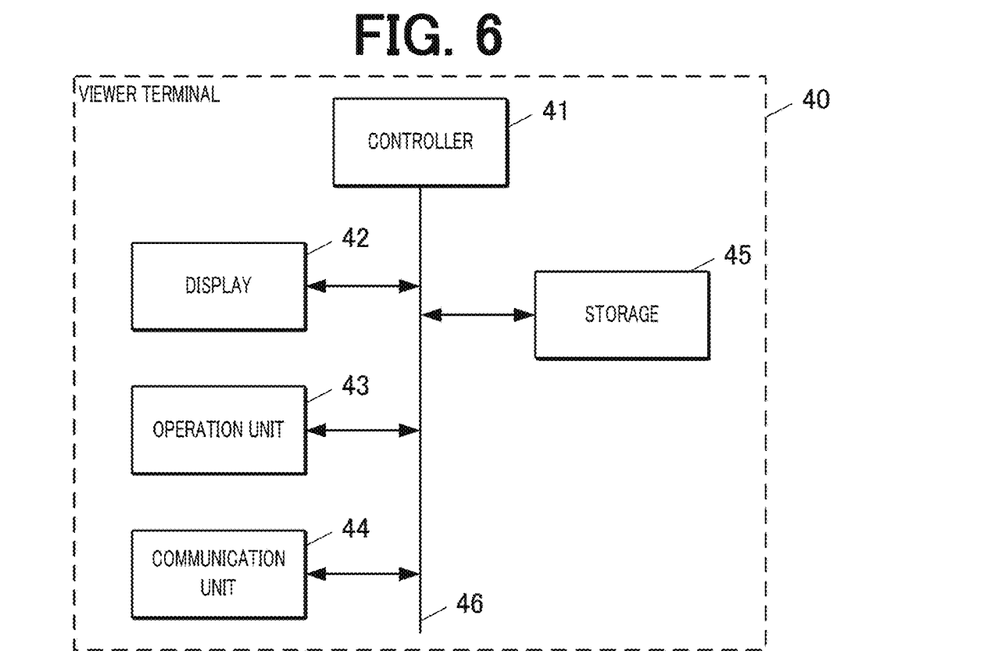
FIG. 6 is a block diagram showing a functional configuration of a viewer terminal.

The controller 21 causes the medical file (the examination image file and the file converted to image) corresponding to the examination selected via the operation unit 43 of the viewer terminal 40 (see FIG. 6) to be displayed in the same screen in the display 42 of the viewer terminal 40 (see FIG. 6).

The non-image file conversion apparatus 30 converts the non-image file related to examination into a file in a format that can be saved in the image storage apparatus 20, and includes a computer device such as a PC (Personal Computer).

Figure 5:
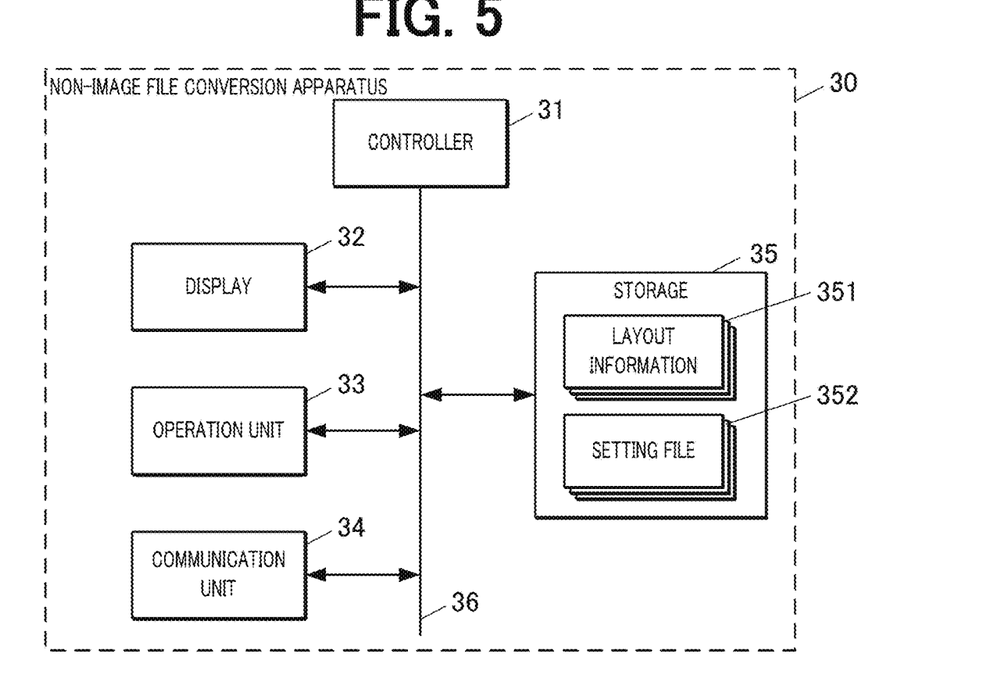
FIG. 5 is a block diagram showing a functional configuration of a non-image fileconversion apparatus.

FIG. 5 shows a functional configuration of the non-image file conversion apparatus 30.

As shown in FIG. 5, the non-image file conversion apparatus 30 includes a controller 31 (first hardware processor), a display 32, an operation unit 33, a communication unit 34, a storage 35, and the like, and these components are connected to one another via a bus 36.

The controller 31 includes a CPU, a ROM, and a RAM and comprehensively controls operation of each component of the non-image fileconversion apparatus 30. Specifically, the CPU reads out various programs stored in the ROM, loads them into the RAM, and performs various processes in accordance with the programs.

The display 32 includes a monitor, such as an LCD (Liquid Crystal Display), where various screens are displayed in accordance with commands of display signals input from the controller 31.

The operation unit 33 includes a keyboard including cursor keys, character/number input keys, and various function keys and a pointing device such as a mouse. Operation signals are input corresponding to key operation on the keyboard or mouse operation and then output to the controller 31.

The communication unit 34 is constituted by a network interface or the like, and sends and receives data to and from an external apparatus(es) connected via the communication network N.

The storage 35 includes an HDD, a non-volatile semiconductor memory, and the like, and stores various kinds of data. The storage 23 stores, for example, layout information 351 and a setting file 352.

The layout information 351 is information used when generating image data from a non-image file, and position information, color, font, size, and the like are set for each item displayed as a character(s). The layout information 351 is prepared in advance for each type of the non-image file(s) (treatment plan information, dose information, and the like) to be processed.

Among the character information included in the non-image file, the item, position information, color, size, shape, and the like are defined in the setting file 352 and used in generating a graph, diagram, or image from numerical data. The "shape" is a shape of the graph, the diagram, or an entire image, and can be designated to be a circle, a rectangle, or the like. The setting file 352 is prepared in advance for each type of the non-image file(s) (treatment plan information, dose information, and the like) to be processed.

The controller 31 generates image data from the character information included in the non-image file related to the examination, attaches the examination information related to the non-image file to the generated image data, and creates the file converted to image (a file in a DICOM format). That is, the controller 31 functions as a creating unit.

The controller 31 generates the image data based on the layout information 351 in which items are associated with position information in advance, specifically by arranging, according to the position information corresponding to the items, the values corresponding to respective items included in the character information obtained from the non-image file.

Furthermore, the controller 31 generates the image data based on the layout information 351 by displaying the values corresponding to respective items included in the character information obtained from the non-image file with the color, font, and size corresponding to the items.

The controller 31 generates a graph, diagram, or image from the character information obtained from the non-image file according to the setting file 352, and embeds the generated graph, diagram, or image in the image data. The controller 31 may generate the graph, diagram or image as a separate layer. Alternatively, the controller 31 may replace the pixel data at a position where the graph, diagram, or image is to be placed in the image data with the data representing the graph, diagram, or image.

The controller 31 sends the created file converted to image to the image storage apparatus 20 via the communication unit 34. That is, the controller 31 and the communication unit 34 function as a sending means.

The controller 31 obtains the examination information from the image storage apparatus 20 based on the character information obtained from the non-image file, and attaches the obtained examination information to the image data. The examination information obtained from the image storage apparatus 20 may be the examination instance UID or the like.

The viewer terminal 40 is a computer device such as a PC used by a doctor. The doctor browses the medical file related to the examination at the viewer terminal 40.

FIG. 6 shows a functional configuration of the viewer terminal 40.

As shown in FIG. 6, the viewer terminal 40 includes a controller 41, a display 42, an operation unit 43, a communication unit 44, a storage 45, and the like, and these components are connected to one another via a bus 46.

The controller 41 includes a CPU, a ROM, and a RAM and comprehensively controls operation of each component of the viewer terminal 40. Specifically, the CPU reads out various programs stored in the ROM, loads them into the RAM, and performs various processes in accordance with the programs.

The display 42 includes a monitor, such as an LCD, where various screens are displayed in accordance with commands of display signals input from the controller 41.

The operation unit 43 includes a keyboard including cursor keys, character/number input keys, and various function keys and a pointing device such as a mouse. Operation signals are input corresponding to key operation on the keyboard or mouse operation and then output to the controller 41.

The communication unit 44 is constituted by a network interface or the like, and sends and receives data to and from an external apparatus(es) connected via the communication network N.

The storage 45 includes an HDD, a non-volatile semiconductor memory, and the like, and stores various kinds of data.

Next, operation of the medical information management system 100 will be described.

Figure 7:
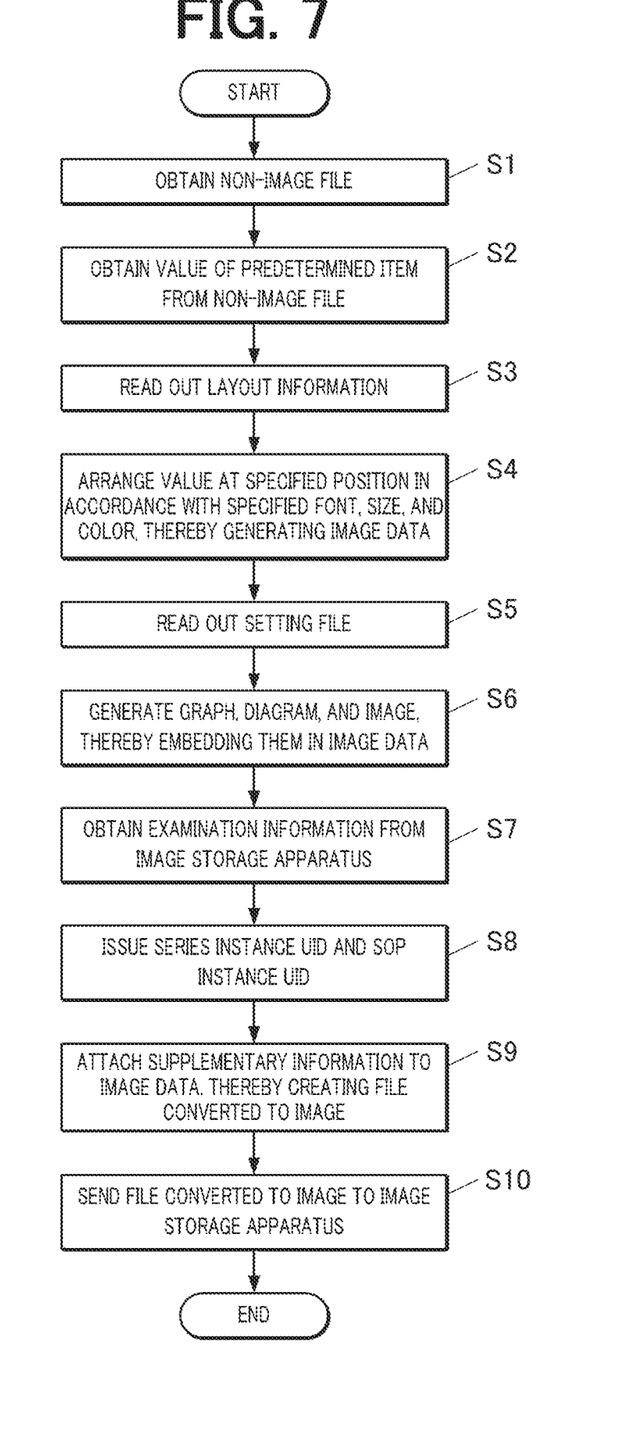
FIG. 7 is a flowchart of non-image file conversion processing that is performed by the non-image file conversion apparatus.

FIG. 7 is a flowchart of the non-image file conversion processing that is performed by the non-image file conversion apparatus 30

First, the controller 31 obtains the non-image file from the examination apparatus 10 or an external device other than the examination apparatus via the communication unit 34 (step S1). The non-image file may be a file in a DICOM format (a header only), a text file, or the like.

Next, the controller 31 obtains the value(s) (character information) of a predetermined item(s) from the non-image file (step S2).

Next, the controller 31 reads out the layout information 351 from the storage 35 (step S3).

FIG. 8 shows an example of the layout information 351. In the layout information 351, for example, a DICOM tag 51, a display format 52, and character setting information 53 are associated with an item name 50 "TREATMENT DATE AND TIME." The DICOM tag 51 is a DICOM tag corresponding to the "treatment date" and "treatment time", and used in specifying the value of the predetermined item(s) (treatment date, treatment time) from the character information included in the non-image file. The display format 52 is a format used in converting the value(s) of the predetermined item(s) specified based on the DICOM tag 51 into image data. For example, a display format such as "YYYY/MM/DD" in which the year, month, and day are separated by "/" is set to be used for the item indicating the date. The character setting information 53 includes a position, font, size, color, and the like in arranging the character(s) (value(s)) of the "treatment date and time" converted into image data.

Next, the controller 31 arranges the value(s) of respective items at the designated position in accordance with the designated font, size, and color, thereby generating image data on the basis of the layout information 351 (step S4).

Figure 9:
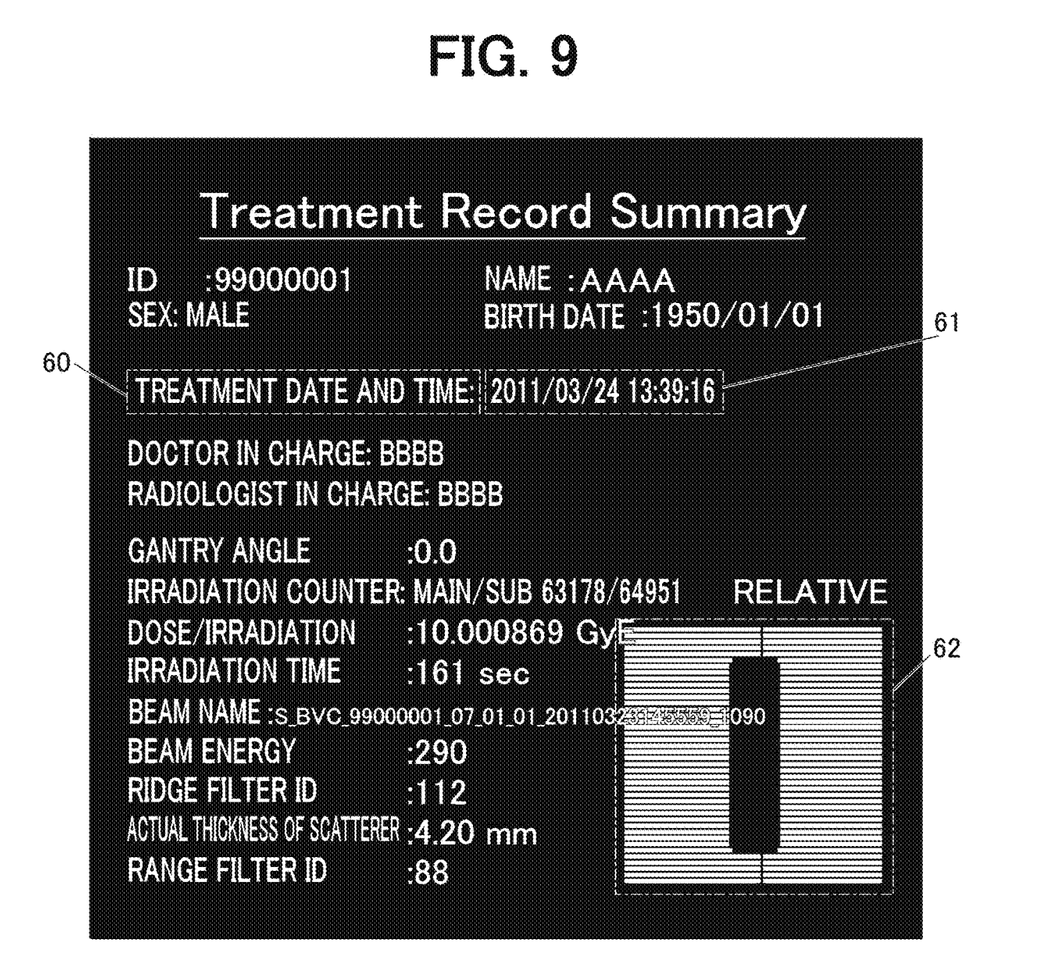
FIG. 9 shows an example of image data generated from character information included in the non-image file.

FIG. 9 shows an example of the image data generated from the character information included in the non-image file (dose information). In an item name region 60, the controller 31 arranges the character "TREATMENT DATE AND TIME" obtained from the item name 50 in the layout information 351 (FIG. 8). In a value region 61, the controller 31 arranges, among the character information included in the non-image file, the value(s) of the item(s) specified based on the DICOM tag 51 in the layout information 351 according to the display format 52 and the character setting information 53 in the layout information 351. The positions of the item name area 60 and the value region 61 are designated in the character setting information 53 of the layout information 351.

Next, the controller 31 reads out the setting file 352 from the storage 35 (step S5).

Figure 10:
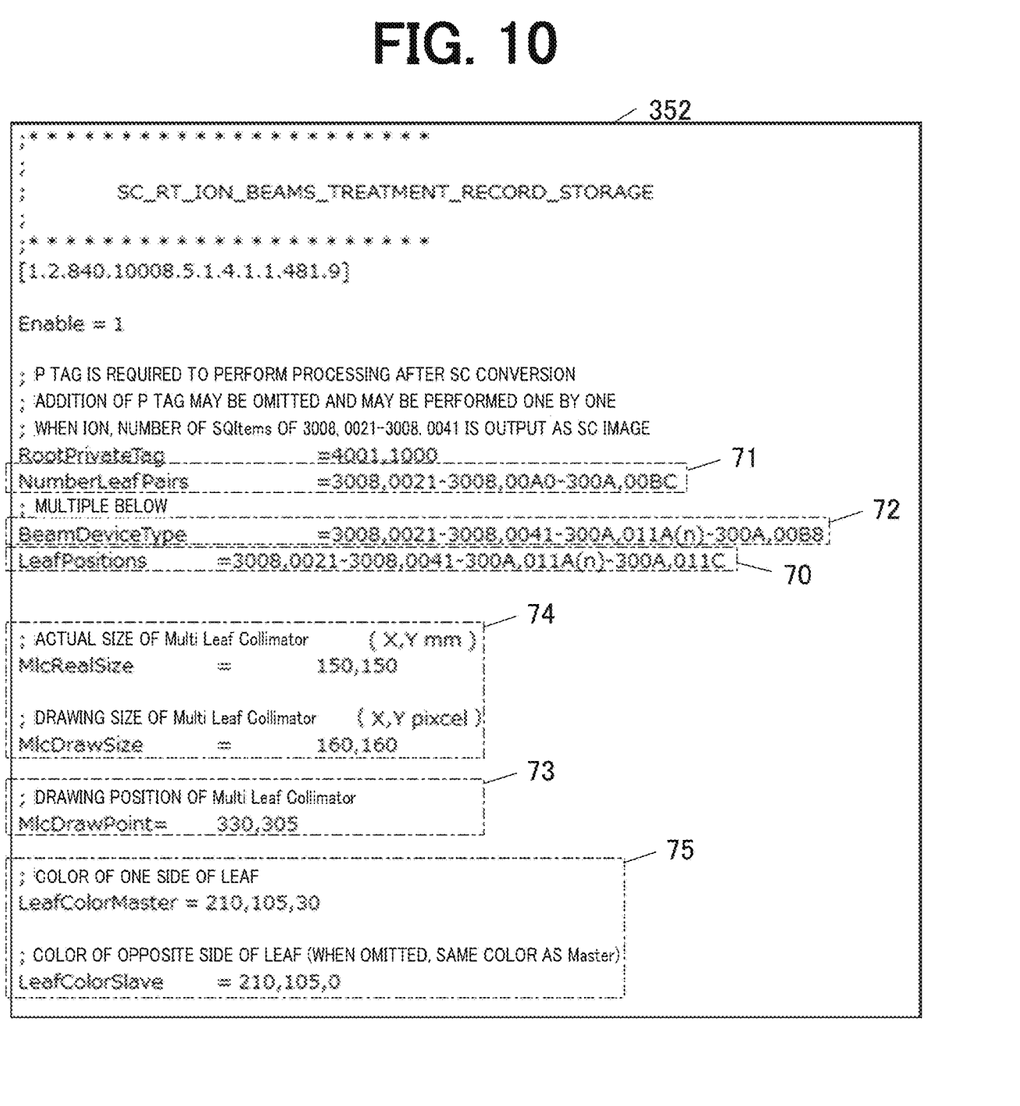
FIG. 10 shows an example of a setting file.

FIG. 10 shows an example of the setting file 352. In the setting file 352, DICOM tag 70 for specifying the item value, DICOM tag 71 for specifying the number of leaf pairs, DICOM tag 72 for specifying the RT beam limiting device type, drawing position 73, drawing size 74, drawing color 75, and the like are associated with the item(s) (here, leaf position) that is among the character information included in the non-image file and embedded in the image data as a graph(s), diagram(s), and image(s).

The DICOM tag 70 is a DICOM tag corresponding to the "leaf position", and is used when the value of a predetermined item (leaf position) is specified from the character information included in the non-image file. A leaf is a metal plate that shields radiation and forms an irradiation field that matches the shape of tumor or the like to protect the patient from radiation by preventing body parts that require no exposure to radiation from being exposed to radiation. The DICOM tag 70 represents usage of the value of (300A, 011C) in (300A, 011A) in (3008, 0041) in the DICOM tag of (3008, 0021). At the time of examination, the position of each leaf is adjusted by the multi-leaf collimator included in the examination apparatus 10.

The DICOM tag 71 is a DICOM tag corresponding to a "number of leaf pairs." The "number of leaf pairs" is the number of leaf pairs arranged on both sides of the midline.

The DICOM tag 72 is a DICOM tag corresponding to the "RT beam limiting device type." The "RT beam limiting device type" is information indicating whether the leaf arrangement is designated based on an X-axis (MLCX) or a Y-axis (MLCY). In the MLCX, the shielding range with the leaf is determined along the X-axis (left-right direction). In the MLCY, the shielding range with the leaf is determined along the Y-axis (upper-lower direction).

The position, size, and color (left/right) are respectively set in the drawing position 73, the drawing size 74, and the drawing color 75 and are used to draw a diagram (leaf diagram) representing leaves formed by the multi-leaf collimator.

Next, the controller 31 generates the graph, diagram, and image from the character information included in the non-image file according to the designated position, size, and color based on the setting file 352, thereby embedding the graph, diagram, and image in the image data (step S6). Which item of the character information included in the non-image file is to be used to generate the graph, diagram, or image is determined in advance depending on which device the non-image file is received from.

For example, the controller 31 generates a leaf diagram and embeds the leaf diagram in the diagram region 62 of the image data shown in FIG. 9.

Figure 11:
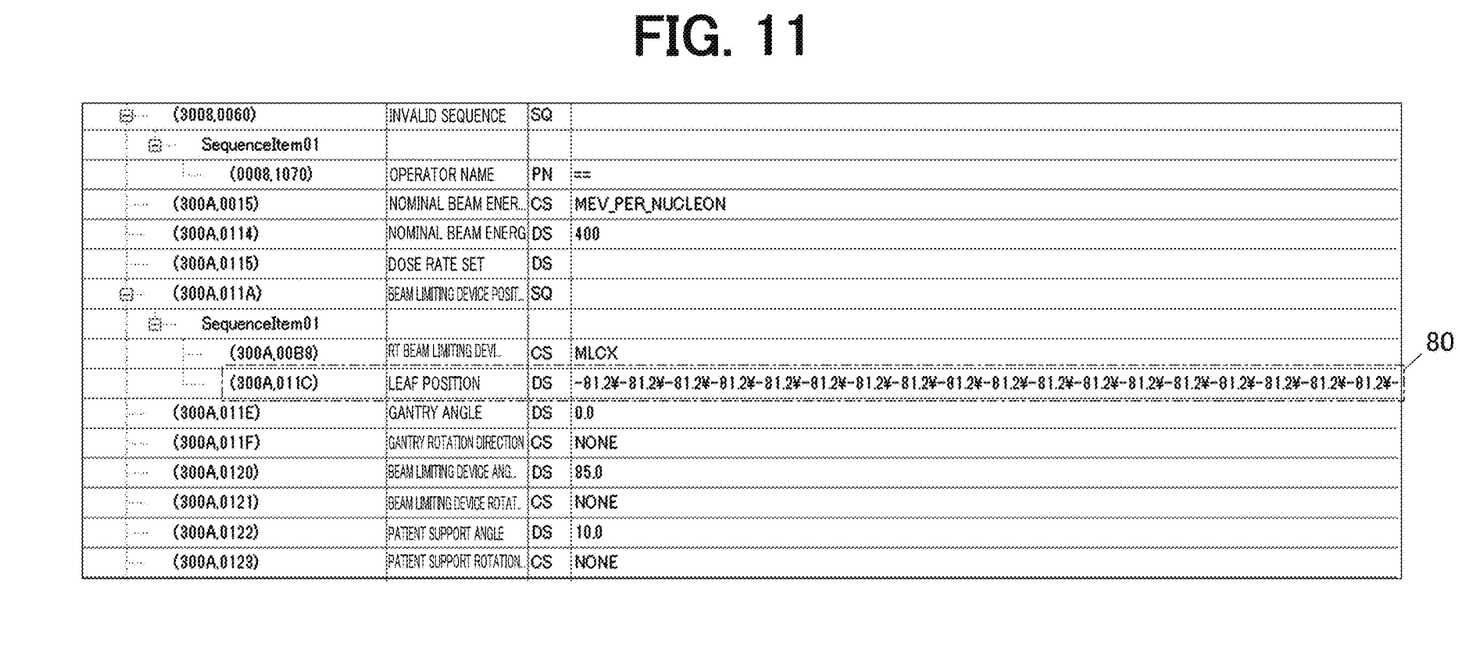
FIG. 11 is a diagram showing an excerpt of a content obtained by analyzing information in a DICOM header of the non-image file for each tag.

FIG. 11 shows an excerpt of the content obtained by analyzing the information in the DICOM header of the non-image file for each tag. The controller 31 generates a leaf diagram based on the value 80 specified with the DICOM tag (300A, 011C) in FIG. 11. In the value 80, numerical values delimited by "Y" represent the respective positions of the leaves.

Figure 12:
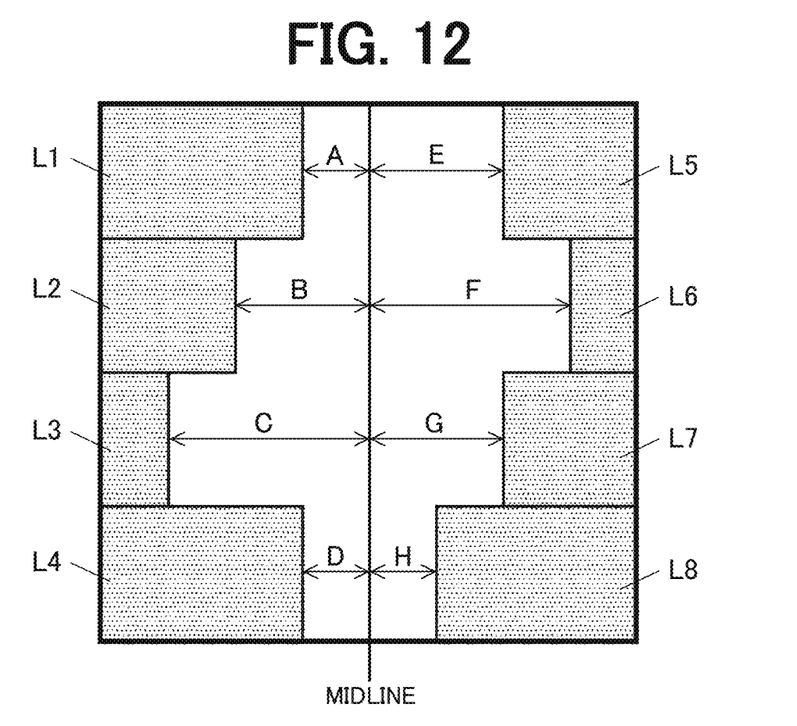
FIG. 12 is a diagram to describe a method of generating a leaf diagram.

Here, with reference to FIG. 12, a method of generating a leaf diagram will be described. When the number of leaf pairs (the value of the DICOM tag designated as NumberLeafPairs) is "4," the RT beam limiting device type (the value of the DICOM tag designated as BeamDeviceType) is "MLCX," and the leaf position (the value of the DICOM tag designated as LeafPositions) is "AYBYCYDYEYFYGYH," as shown in FIG. 12, The values A to H represent the distances from the inner ends of the leaves L1 to L8 to the midline. Specifically, the values A to D are the X coordinates of the right ends of the left leaves L1 to L4, and the values E to H are the X coordinates of the left ends of the right leaves L5 to L8. Regions between the leaf pairs (left and right leaves) determined by the values A to H are irradiated with radiation.

When the non-image file does not include information indicating the leaf position, no leaf diagram is generated.

Next, the controller 31 obtains examination information (including examination instance UID) from the image storage apparatus 20 on the basis of the character information obtained from the non-image file (step S7).

The controller 31 obtains, for example, the patient name, birth date, sex, examination instance UID, and the like from the image storage apparatus 20 using the patient ID, examination date, and modality included in the non-image file as search conditions.

Next, in accordance with the DICOM standard, the controller 31 issues the series instance UID and SOP instance UID (step S8) to the non-image file to be processed that has been converted to image data.

Next, the controller 31 attaches supplementary information to the image data (image data generated in step S4 in which graph, diagram, or image is embedded in step S6), thereby creating the file converted to image (a file in a DICOM format) (step S9). Specifically, the controller 31 writes supplementary information in the header, such as the character information obtained from the non-image file, the examination information obtained from the image storage apparatus 20, and the series instance UID and the SOP instance UID issued in step S8, thereby creating the file converted to image.

Next, the controller 31 sends the file converted to image to the image storage apparatus 20 via the communication unit 34 (step S10).

The non-image file conversion processing is completed as described above.

In the image storage apparatus 20, when the communication unit 22 receives the file converted to image from the non-image file conversion apparatus 30, the controller 21 specifies the target examination by obtaining the examination instance UID from the header of the file converted to image. The controller 21 creates, in a folder layer under the "examination instance UID" folder corresponding to the specified examination in the file storage region 232 of the storage 23, a "series instance UID" folder named after the series instance UID included in the header of the file converted to image. The controller 21 stores the file converted to image in a folder layer under the "series instance UID" folder. The controller 21 further obtains various kinds of information from the header of the received file converted to image and saves the information in the image management DB 231.

Figure 13:
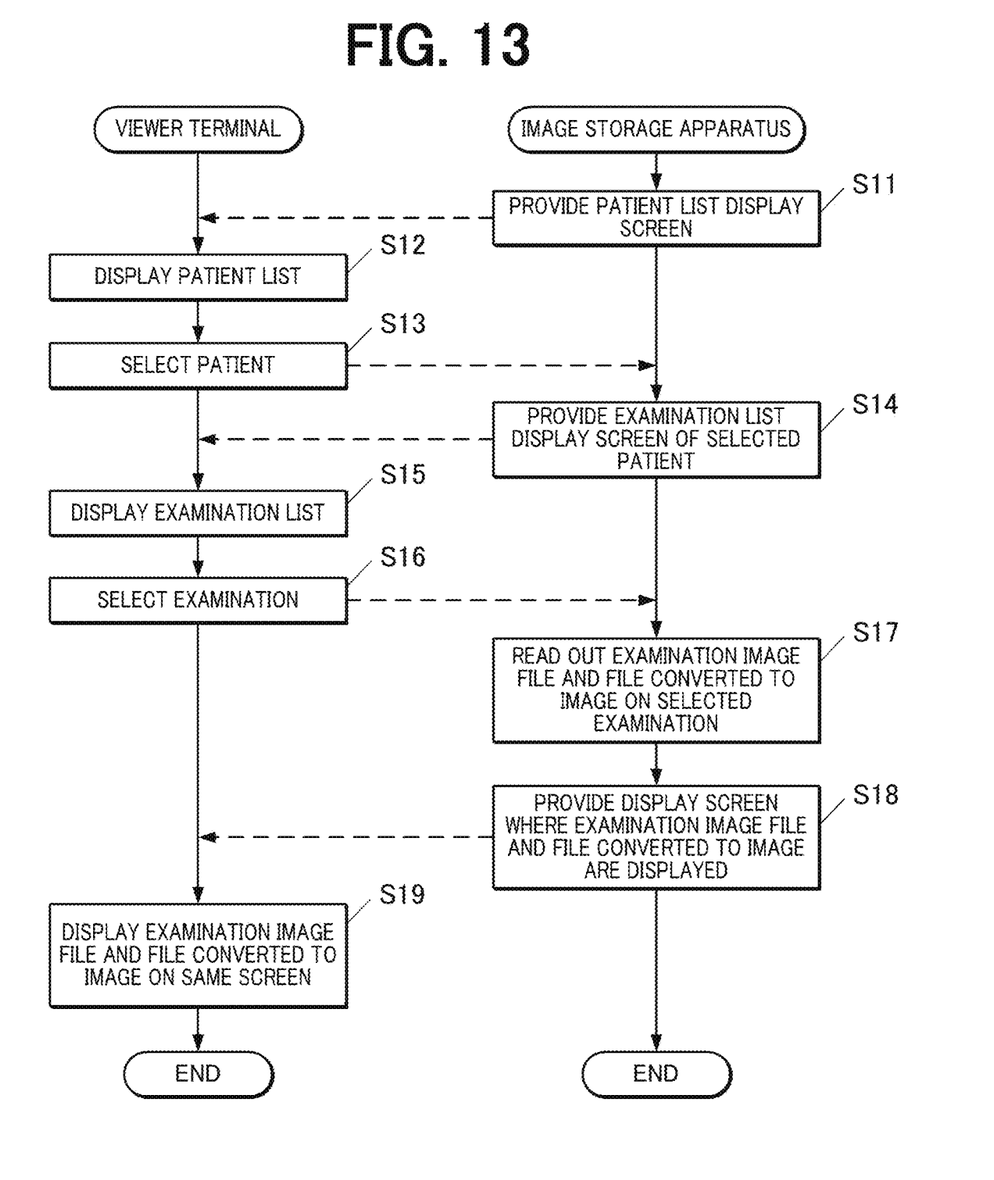
FIG. 13 is a ladder chart showing examination browsing processing performed by the viewer terminal and the image storage apparatus.

FIG. 13 is a ladder chart showing examination browsing processing performed by the viewer terminal 40 and the image storage apparatus 20.

First, the controller 21 of the image storage apparatus 20 refers to the image management DB 231 of the storage 23, generates a display screen of a patient list on the basis of the saved patient information, and provides the patient list display screen to the viewer terminal 40 via the communication unit 22 (step S11).

In the viewer terminal 40, the patient list is displayed on the display 42 (step S12).

When the user selects a patient from the patient list by operating the operation unit 43 of the viewer terminal 40 (step S13), the controller 21 of the image storage apparatus 20 refers to the image management DB 231 of the storage 23, generates a examination list display screen on the basis of the examination information related to the selected patient, and provides the display screen to the viewer terminal 40 via the communication unit 22 (step S14).

In the viewer terminal 40, the examination list is displayed on the display 42 (step S15).

When the user selects an examination from the examination list by operating the operation unit 43 of the viewer terminal 40 (step S16), the controller 21 of the image storage apparatus 20 reads out the examination image file and the file converted to image on the selected examination (step S17). Specifically, the controller 21 reads out, from the file storage region 232 of the storage 23, the medical files (the examination image file and the file converted to image) stored in a folder layer under the "examination instance UID" folder corresponding to the selected examination.

The controller 21 generates a display screen where the examination image file and the file converted to image related to the selected examination are simultaneously displayed, and provides the display screen to the viewer terminal 40 via the communication unit 22 (step S18).

In the viewer terminal 40, the examination image file and the file converted to image are displayed in the same screen of the display 42 (step S19).

Figure 14:
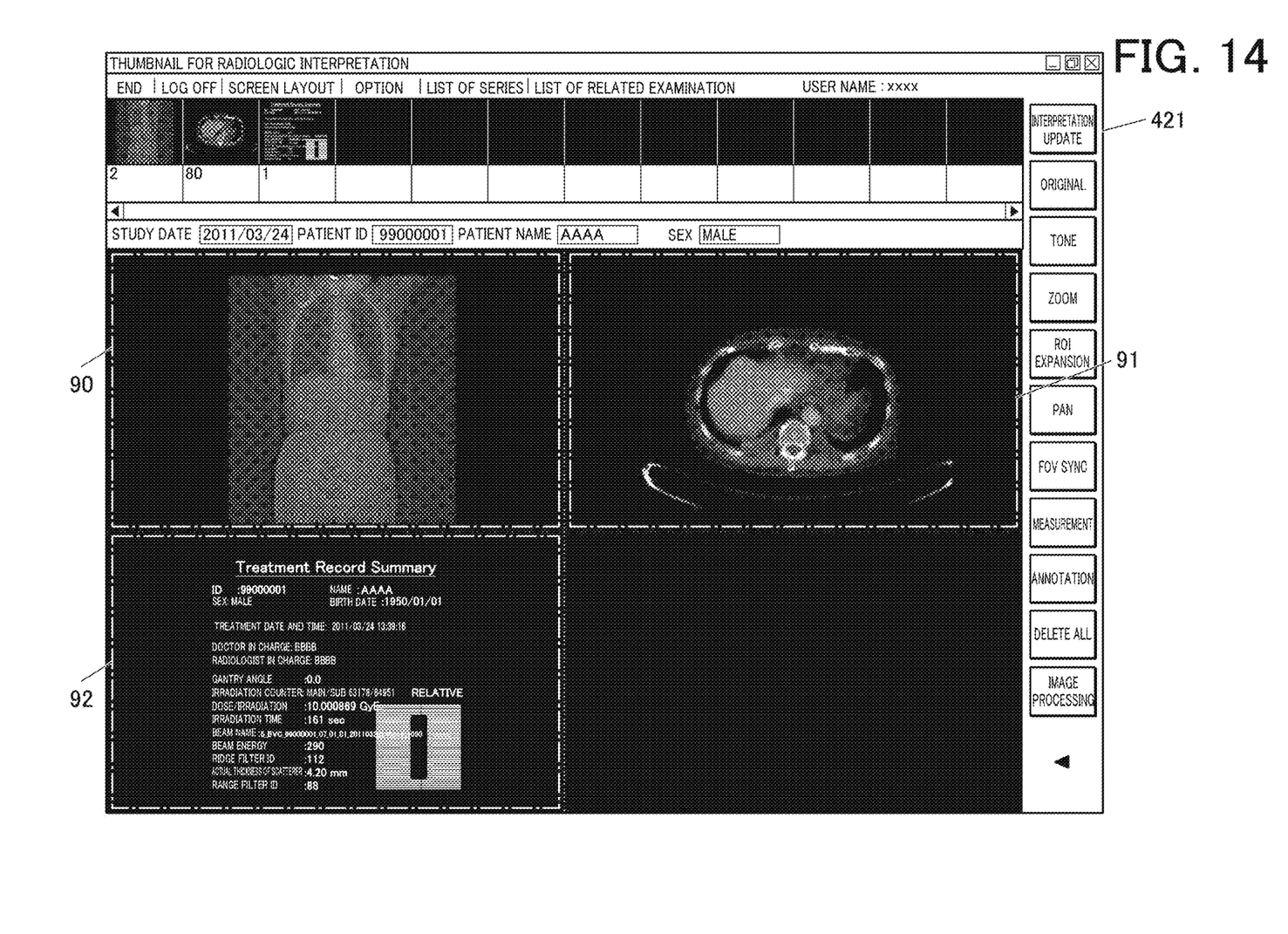
FIG. 14 shows an example of an examination browsing screen that is displayed by the viewer terminal.

FIG. 14 shows an example of the examination browsing screen 421 that is displayed on the display 42 of the viewer terminal 40. The examination browsing screen 421 includes the examination image files 90, 91 and the file converted to image 92 related to the selected examination.

The examination browsing processing is completed as described above.

As described above, according to the present embodiments, in the non-image file conversion apparatus 30, image data is generated from the character information included in the non-image file related to the examination, and the examination information related to the non-image file is attached to the generated image data, thereby creating the file converted to image. Accordingly, the non-image file related to an examination can be managed in association with the corresponding examination.

Furthermore, based on the layout information 351, the values corresponding to respective items included in the character information are arranged according to the position information corresponding to the items. Therefore, it is possible to generate image data in which the values corresponding to the respective items are arranged at positions determined in advance.

Furthermore, because the values corresponding to respective items are displayed with the color, font, or size corresponding to the items. For example, when the color, font or size is changed depending on the items, the property of data can be visualized, thereby preventing erroneous recognition.

Furthermore, since a graph, diagram, or image is generated from the character information, it is easy to visually recognize the character information. Furthermore, by changing the shape, color, or size of the graph, diagram, or image embedded in the image data, it is possible to display the screen as desired by the user.

Furthermore, examination information (such as the examination instance UID) is obtained from the image storage apparatus 20 on the basis of the character information included in the non-image file, and is attached to the image data generated from the non-image file. Therefore, it can be easily associated with the relevant examination.

In the non-image file conversion apparatus 30, the non-image file is converted into a file in a format that the image storage apparatus 20 can handle (file converted to image) and then sent to the image storage apparatus 20. Therefore, in the image storage apparatus 20, the file converted to image can be managed for each examination as well as the examination image file. In this way, the image storage apparatus 20 can store the file converted to image and the related examination image as the same examination. The image storage apparatus 20 causes the examination image file and the file converted to image related to the selected examination to be displayed in the same screen of the viewer terminal 40. Therefore, it is possible to prevent overlooking of the file converted to image (the data that is originally a non-image file).

The description in the above embodiment is an example of the medical information management system according to the present invention, and the present invention is not limited to this. The detailed configuration and detailed operation of each unit that constitutes each device can be appropriately changed without departing from the spirit of the present invention.

For example, in the non-image file conversion processing (see FIG. 7), step S7 may be omitted if the examination instance UID can be obtained from the character information of the non-image file.

Furthermore, depending on the imaging conditions of the examination image in the examination apparatus 10, the non-image file conversion apparatus 30 may start the non-image file conversion processing before the image storage apparatus 20 imports the examination image file. In such a case, the non-image file conversion apparatus 30 may monitor the import of the examination image file for the relevant examination by the image storage apparatus 20, so as to perform the processes from step S7 of the non-image file conversion processing after the image storage apparatus 20 has finished importing the examination image file.

In the above described example, ROM is used as a computer readable medium that stores the programs to perform the processing. However, the present invention is not limited to this example. A portable storage medium such as a non-volatile flash memory and a CD-ROM can also be used as the computer readable medium. Further, as a medium to provide data of the programs of the present disclosure via a communication line, a carrier wave can be used. Other examples of applicable computer-readable medium include a non-volatile memory such as a flash memory, a portable recording medium such as CD-ROM, and the like. Furthermore, a carrier wave can be used as a medium to provide data of the programs of the present disclosure via a communication line.

Although embodiments of the present invention have been described and illustrated in detail, the disclosed embodiments are made for purposes of illustration and example only and not limitation. The scope of the present invention should be interpreted by terms of the appended claims.

What is claimed is:

1. An information processing apparatus that sends and receives data to and from an image storage apparatus that manages a medical file for each of at least one examination, the information processing apparatus comprising:
   a storage storing layout information, the layout information defining a predetermined association between (i) a predetermined item of examination information, the predetermined item including character information, and (ii) position information indicating a display position of the predetermined item within a file converted to image; and
   a first hardware processor that:
     generates image data from character information included in a non-image file related to an examination, for each predetermined item of examination information included in the non-image file, such that a value corresponding to the predetermined item is arranged in the generated image data at a position corresponding to its associated position information in the layout information;
     attaches examination information related to the non-image file to the generated image data;
     creates the file converted to image based on the generated image data and the examination information attached thereto; and
     sends the created file converted to image to the image storage apparatus.

2. The information processing apparatus according to claim 1 Pa wherein:
   the predetermined item is further associated with a predetermined color, font, or size in the layout information, and
   the first hardware processor generates the image data based on the layout information by representing the value corresponding to the predetermined item included in the character information with the color, font, or size with which the predetermined item is associated.

3. The information processing apparatus according to claim 1, wherein the first hardware processor generates a graph, diagram, or image from the character information and embeds the generated graph, diagram, or image in the image data.

4. The information processing apparatus according to claim 1, wherein the first hardware processor obtains the examination information from the image storage apparatus based on the character information, and attach attaches the obtained examination information to the image data.

5. A medical information management system comprising:
- the information processing apparatus according to claim 1; and
- the image storage apparatus,
- wherein:
  - the medical file managed by the image storage apparatus includes (i) an examination image file that is taken during examination of a patient and (ii) the file converted to image that is created by the information processing apparatus, and
  - the image storage apparatus includes a second hardware processor that causes the examination image file and the file converted to image corresponding to an examination selected via an operation unit to be displayed in a same screen of a display.

6. An information processing method that is performed in an information processing apparatus that sends and receives data to and from an image storage apparatus that manages a medical file for each of at least one examination, the method comprising:
- storing layout information, the layout information defining a predetermined association between (i) a predetermined item of examination information, the predetermined item including character information, and (ii) position information indicating a display position of the predetermined item within a file converted to image;
- generating image data from character information included in a non-image file related to an examination, for each predetermined item of examination information included in the non-image file, such that a value corresponding to the predetermined item is arranged in the generated image data at a position corresponding to its associated position information in the layout information;
- attaching examination information related to the non-image file to the generated image data;
- creating the file converted to image based on the generated image data and the examination information attached thereto; and
- sending the created file converted to image to the image storage apparatus.

7. The information processing apparatus according to claim 3, wherein the first hardware processor embeds the generated graph, diagram, or image in the image data by replacing a portion of pixel data included in the image data with pixel data representing the generated graph, diagram, or image.

8. The information processing apparatus according to claim 5, wherein the file converted to image is a file that is separate from the examination image file and that is stored in association with the examination image file.

* * * * *